United States Patent
Alzugaray

(10) Patent No.: US 7,494,471 B2
(45) Date of Patent: Feb. 24, 2009

(54) MOON PHASE MENSTRUAL TRACKING AND EDUCATIONAL SYSTEM

(76) Inventor: Marina Alzugaray, 638 Caribbean Dr. East, Summerland Key, FL (US) 33042

( * ) Notice: Subject to any disclaimer, the term of this patent is extended or adjusted under 35 U.S.C. 154(b) by 49 days.

(21) Appl. No.: 11/049,030

(22) Filed: Feb. 1, 2005

(65) Prior Publication Data
US 2006/0173376 A1    Aug. 3, 2006

(51) Int. Cl.
A61B 10/00 (2006.01)
G04B 19/26 (2006.01)
G01N 33/48 (2006.01)
B42D 5/04 (2006.01)
B42D 15/00 (2006.01)
G09B 29/00 (2006.01)
G09B 19/02 (2006.01)
G09B 23/02 (2006.01)

(52) U.S. Cl. .................. 600/551; 968/207; 968/208; 968/209; 968/210; 368/16; 368/18; 436/65; 283/2; 283/34; 283/44; 283/115

(58) Field of Classification Search .................. 600/551; 968/207, 208, 209, 210; 368/16, 18; 436/65; 283/2, 34, 44, 115
See application file for complete search history.

(56) References Cited

U.S. PATENT DOCUMENTS

| | | | |
|---|---|---|---|
| 4,131,790 A | 12/1978 | Rebsch | |
| 4,273,337 A | 6/1981 | Carrera et al. | |
| 4,350,878 A | 9/1982 | Schwarz et al. | |
| 4,381,121 A | 4/1983 | Hanley | |
| 4,480,840 A | 11/1984 | Chang | |
| 4,670,401 A | 6/1987 | Cutler et al. | |
| 4,788,984 A * | 12/1988 | Marsik | 600/551 |
| 4,879,244 A | 11/1989 | Cutler et al. | |
| 5,043,888 A | 8/1991 | Uriarte | |
| 5,215,309 A | 6/1993 | Joel | |
| 5,306,007 A | 4/1994 | Scuteri | |
| 5,310,994 A | 5/1994 | Thabet et al. | |
| 5,313,722 A | 5/1994 | Ackerman | |
| D351,414 S | 10/1994 | Buhner | |

(Continued)

OTHER PUBLICATIONS

"2005 Lunar Phases," 1 page (2004).

(Continued)

Primary Examiner—Max Hindenburg
Assistant Examiner—Jeffrey G Hoekstra
(74) Attorney, Agent, or Firm—Pauly, DeVries Smith & Deffner, L.L.C.

(57) ABSTRACT

A system and method for tracking and informing about a physical, emotional, or physiological cycle, such as a menstrual cycle, includes at least one definition entry and at least one date indicator. Each definition entry defines indicia such as color to represent a stage of a physical, emotional, or physiological cycle. Each date indicator includes a date section and a tracking section corresponding to each date section. The date section of the date indicator indicates at least one date, wherein the tracking section is capable of being marked so as to indicate indicia corresponding to a definition entry to signify the stage of the physical, emotional, or physiological cycle for each date. According to one embodiment, the date indicators are arranged according to phases of the moon to allow correlation of a user's cycle to the lunar cycle.

14 Claims, 11 Drawing Sheets
(7 of 11 Drawing Sheet(s) Filed in Color)

U.S. PATENT DOCUMENTS

| | | | |
|---|---|---|---|
| 5,515,344 | A | 5/1996 | Ng |
| 5,533,731 | A | 7/1996 | Koenig |
| 5,606,535 | A | 2/1997 | Lynn |
| 5,636,870 | A | 6/1997 | Enhorning |
| 5,701,678 | A | 12/1997 | Wang |
| 5,903,524 | A | 5/1999 | Clarke |
| 5,954,331 | A | 9/1999 | Hepburn |
| 6,110,125 | A | 8/2000 | Young et al. |
| 6,278,662 | B1 | 8/2001 | Gruber |
| 6,497,718 | B1 | 12/2002 | Dewan |
| 6,545,951 | B1 | 4/2003 | Lynn |
| 6,656,130 | B2 | 12/2003 | Takehara et al. |
| 6,747,917 | B2 | 6/2004 | Jennings et al. |
| 6,886,740 | B1 * | 5/2005 | Craig .................... 235/85 FC |

OTHER PUBLICATIONS

"Everwoman's Calendar," 1 page (1982).

"Great new Products from Childbirth Graphics," 2 pages (available at least as early as Oct. 2004).

"How to Talk with Your Child About Sexuality—A Parent's Guide," 4 pages (May 2002).

"Menstruation—Talking with Your Daughter," 2 pages (1996).

"Points for Parents—About Teenage Growth and Development: 11-14 years," 2 pages (1997).

"Points for Parents—About Teenage Growth and Development: 15-17 years," 2 pages (1997).

"Points for Parents—About Teens and Sex," 2 pages (1997).

"Preparing for Pregnancy," 2 pages (available at least as early as Oct. 2004).

"Suggested Beginning Library", 1 page (available at least as early as Oct. 2004).

Sweeney, K., "Resources for the Menstrual Life Cycles," *Mothering*, pp. 48, 50-54 (Winter 1991).

"Talking to Your Kids about Sex," *American Academy of Child & Adolescent Psychiatry*, No. 62, 2 pages, http://www.aacap.org/publications/factsfam/62.htm (Feb. 1998).

"Talking About Sex—Encouraging Abstinence—Ten Tips for Parents," 2 pages (1998).

"The Facts of Life— Guide for Teens and their Families," pp. 1-29 (Sep. 1999).

"Wemoon.com calendar for Feb. 2004," 2 pages (this example is meant to be illustrative of the we'moon calendar, which has been produced since at least 2002).

"We'Moon '05: Gaia Rhythms for Womyn," 1 page (2004).

Weschler, T., *Taking Charge of Your Fertility. The Definitive Guide to Natural Child Birth Control, Pregnancy Achievement, and Reproductive Health*, 7 pages (2002).

"Your Provider is a Resource for Adolescent Health!" American College of Nurse Midwives and HRSA (4 pages) (at least as early as Oct. 2004).

"Birth Control Chart—Farenheit" *Ovusoft*, http://www.tcoyf.com/library/pdf/bc_fahr.pdf (2001-2002) (master chart from the book by T. Weschler referenced above) (1 page) and website from which the chart is available (2 pages).

* cited by examiner

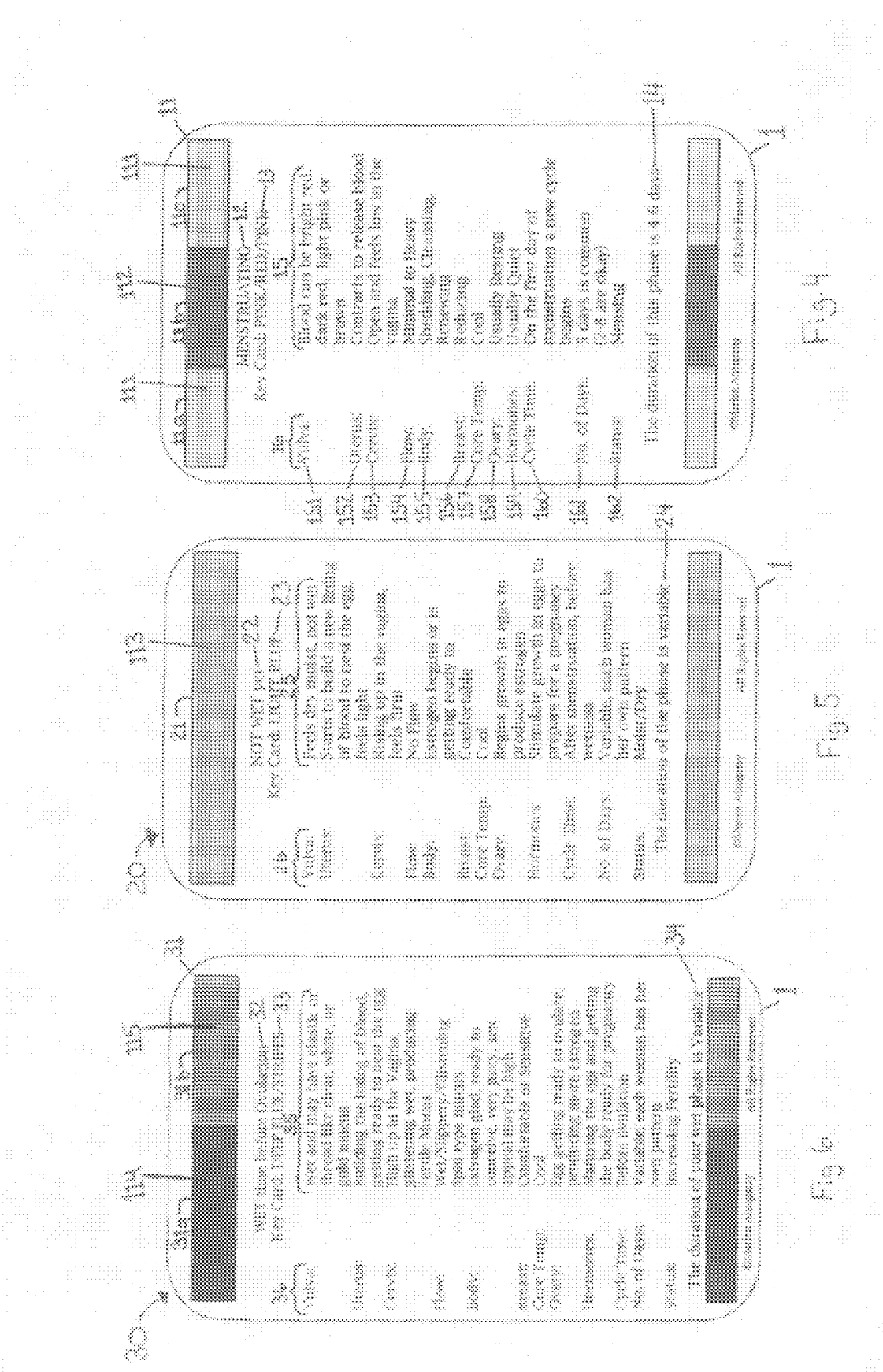

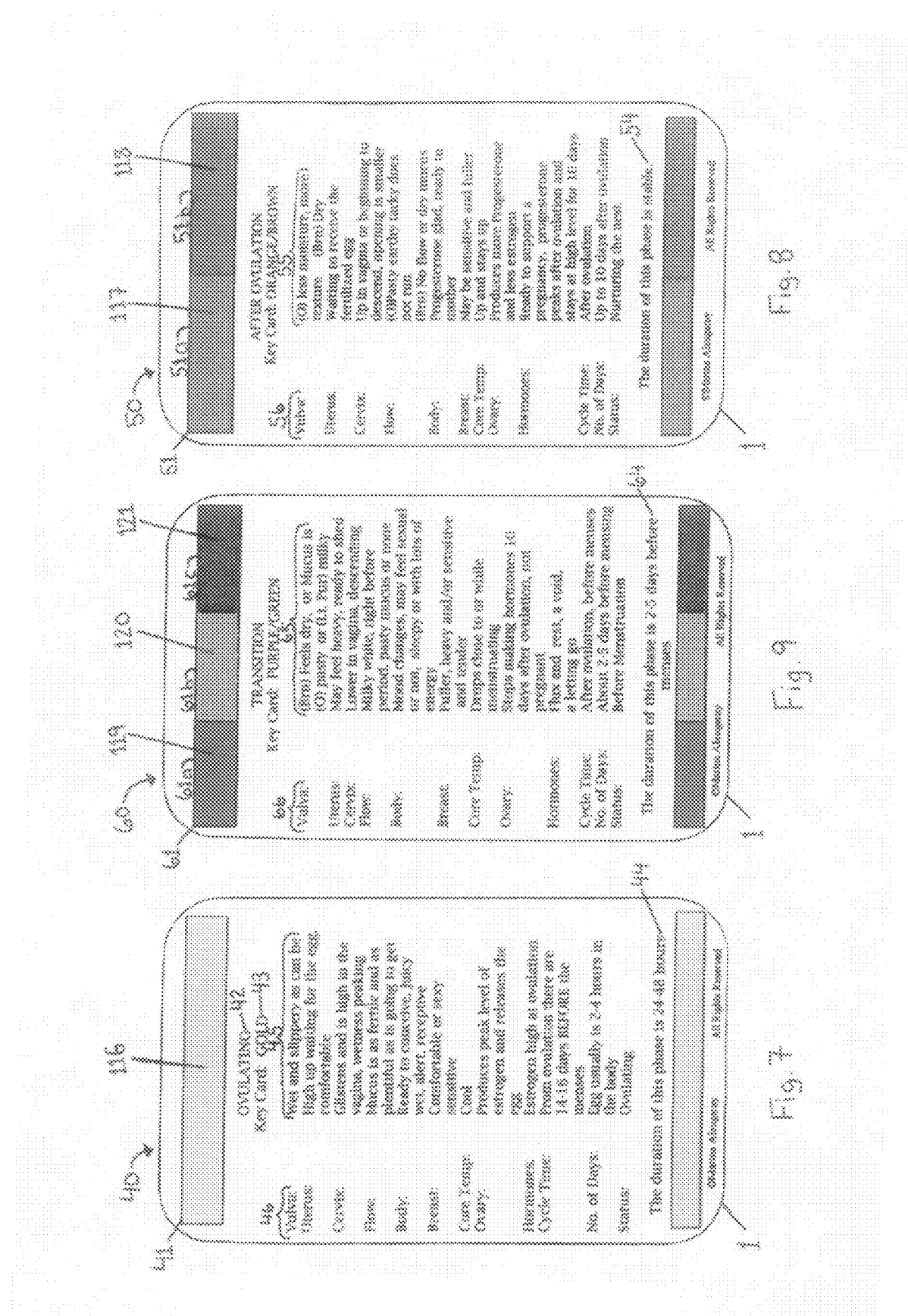

MOON PHASE MENSTRUAL TRACKING AND EDUCATIONAL SYSTEM

TECHNICAL FIELD

The present invention relates to a system and method for educating about and tracking health and body phases and characteristics, and more particularly to a menstrual tracking and educational system and method.

BACKGROUND

One goal of existing menstrual tracking and educational systems and methods is predicting when a woman will ovulate and therefore be likely to conceive a child. Whether used for contraception or conception, these systems and methods are geared towards a woman who is or plans to become sexually active. Some devices involve various indexing devices or calendars that a woman may use to calculate her fertility periods within a given timeframe. See, for example, U.S. Pat. No. 4,381,121 to Hanley. Other devices include watches or other electronic devices that calculate the fertility period down to hours or even minutes. See, for example, U.S. Pat. No. 6,278,662 to Gruber.

In some of these devices, the calculations are based on the onset date of the woman's menses. In other devices, the calculations are based on a small set of physical reactions or hormonal changes the woman is likely to experience when she is approaching or in her fertility period. See, for example, U.S. Pat. No. 4,670,401 to Cutler et al. Other devices focus primarily on predicting the on-set date of the woman's next menses. Still other devices attempt to change the menstrual cycle, delaying menstruation for a short period of time or causing it to occur more regularly. See, for example, U.S. Pat. No. 6,497,718 to Dewan.

Another goal of existing menstrual tracking and educational systems and methods is informing women about the menstrual cycle in general and the changes that typically occur in the female body during each cycle. Some devices have used charts, graphs, books, and other teaching aides to educate women about anatomy, conception, contraception, and menstruation. For example, a product called A Woman's Monthly Carousel is designed as a teaching aide in explaining the female reproductive system. This device includes a rotating carousel, tear pad, and a chart, each depicting hormone levels, basal body temperature, and other such information over an average 28-day menstrual cycle.

Few, if any, of these devices may be personalized to each individual user. Many of these devices are geared towards women who are or are likely to become sexually active. There is a need for improved menstrual tracking and educational systems and methods.

SUMMARY

In general terms, the present invention relates to a system and method for enabling a woman to more easily track and understand her physical and emotional reactions to bodily changes, particularly during her menstrual cycle.

According to one embodiment, the present invention includes a system for tracking and informing about a woman's menstrual cycle. The system includes multiple color definition entries, each color definition entry defining a color as representing a stage of the menstrual cycle. The system further includes multiple date indicators, each date indicator including a date section and a tracking section corresponding to each date section. The date section of the date indicator indicates at least one date, wherein the tracking section is capable of being marked so as to indicate one of the colors for which there is a color definition entry to signify the stage of a woman's menstrual cycle for each date.

According to another embodiment, a system for tracking and informing about a physiological cycle, such as a woman's menstrual cycle includes multiple visual moon phase symbols, each moon phase symbol corresponding to a moon phase. The system further includes a visual list of calendar dates for each moon phase symbol corresponding to the actual occurrence of each moon phase. The system further includes multiple markable areas corresponding to each calendar date where a user can mark information about the user's physiological cycle. In one embodiment for tracking a woman's menstrual cycle, each markable area includes multiple markable sections, each section corresponding to a stage of a menstrual cycle.

According to yet another embodiment, a system for tracking and informing about a woman's menstrual cycle includes a set of key cards, wherein each key card includes textual information about a stage of a menstrual cycle. The system further includes a set of tracking cards, wherein each tracking card includes a visual representation of more than one calendar date and is configured so a user can indicate the user's current menstrual cycle stage on a particular date by marking one of multiple visual representations of stages of a menstrual cycle. The ability to put large amounts of information into an easy to understand and easy to reference format enables the key cards to be useful to a broad audience.

According to still yet another embodiment, a system for tracking and informing about a woman's reproductive system, pregnancy for example, includes a plurality of color definition entries. Each color definition entry defines a color as representing a stage of a reproductive process. The system further includes multiple date indicators, each date indicator including a date section and a tracking section corresponding to each date section. The date section indicates one date, wherein the tracking section is capable of being marked so as to indicate one of the colors for which there is a color definition entry to signify the woman's stage of the reproductive process for each date.

One feature of the present invention is that one embodiment is used to correlate the menstrual cycle to the lunar cycle rather than a Gregorian calendar. The menstrual cycle is generally more similar to the cycles of the moon than to a Gregorian calendar. A woman's womb empties and fills each month like the moon. A calendar is broken into twelve months with each month generally taking 30 to 31 days, whereas a moon phase cycle takes 29 and one half days. The average woman's cycle lasts between 25 and 28 days. The moon revolves around the Earth 13 times a year and a woman ovulates an average of 13 times a year. These similarities are illustrated by one embodiment of the present invention.

BRIEF DESCRIPTION OF THE DRAWINGS

The patent or application file contains at least one drawing executed in color. Copies of this patent or patent application publication with color drawings will be provided by the Office upon request and payment of the necessary fee.

The invention may be more completely understood by considering the detailed description of various embodiments of the invention which follows in connection with the accompanying drawings.

FIG. 4 illustrates an example of a color definition entry, where a menstrual phase is linked to two colors, displayed on a key card according to one embodiment of the present invention.

FIG. 5 illustrates another example of a color definition entry displayed on a key card according to one embodiment of the present invention.

FIG. 6 illustrates another example of a color definition entry displayed on a key card according to one embodiment of the present invention.

FIG. 7 illustrates another example of a color definition entry displayed on a key card according to one embodiment of the present invention.

FIG. 8 illustrates another example of a color definition entry displayed on a key card according to one embodiment of the present invention.

FIG. 9 illustrates another example of a color definition entry displayed on a key card according to one embodiment of the present invention.

Figure 1:
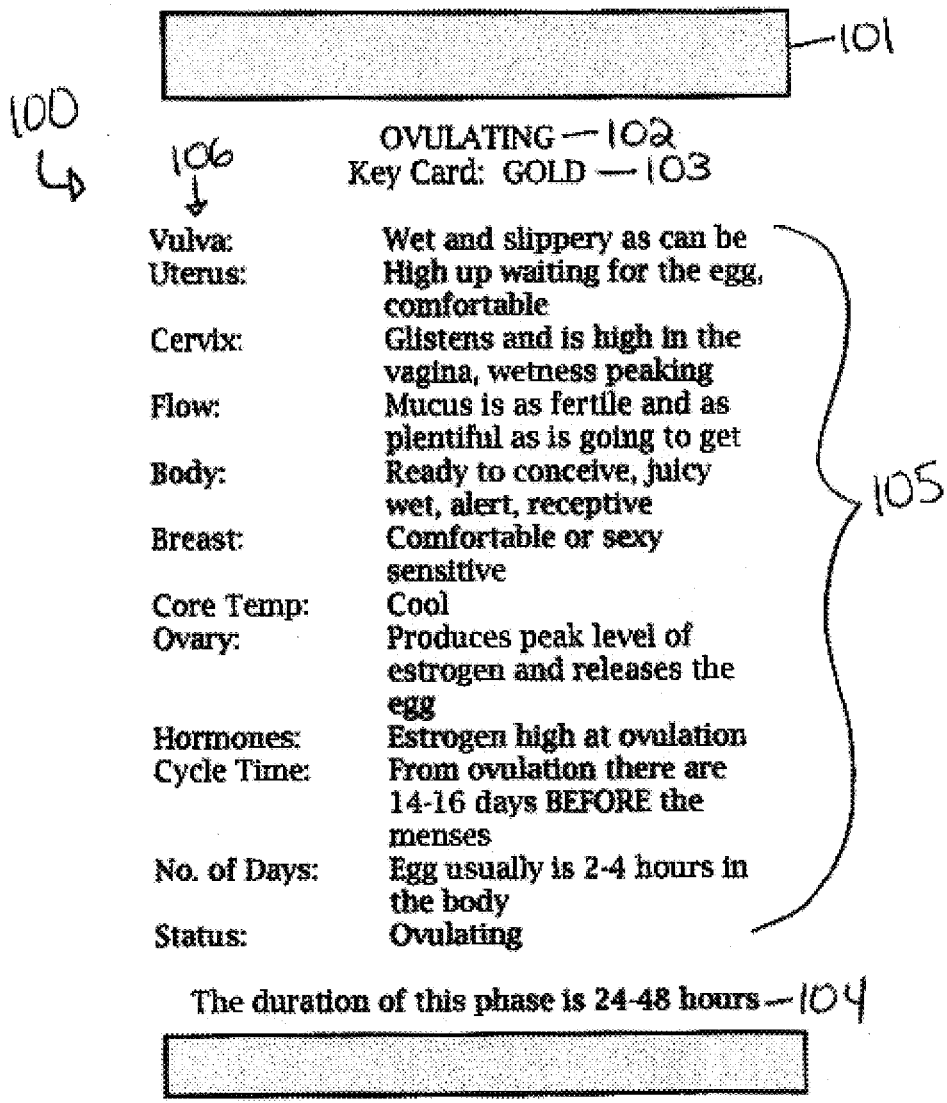
FIG. 1 illustrates a color definition entry according to one possible embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is directed at a system and method for tracking and informing about bodily changes, such as a woman's menstrual cycle. The invention has been found to be particularly advantageous where detailed information is to be conveyed about the phases of a menstrual cycle. Also, the invention has been found to be particularly advantageous for correlating a woman's menstrual cycle with the phases of the moon. While the present invention is not so limited, an appreciation of various aspects of the invention is best gained through a discussion of various application examples operating in these environments.

The present disclosure divides the menstrual cycle into stages. One embodiment of the present disclosure includes a plurality of color definition entries. Each color definition entry assigns a title and a corresponding color or set of colors to each stage of the menstrual cycle. Generally, the menstrual cycle can be split into any number of stages ranging from two to twenty-eight. A two-stage division would typically indicate fertile and not fertile periods. A twenty-eight-stage division would indicate a different stage for each day of the menstrual cycle. According to one embodiment, dividing the menstrual cycle into six stages is logical and instructive.

Referring to FIG. 1, a color definition entry 100 according to one embodiment of the present disclosure is illustrated. The color definition entry 100 includes a color bar 101, a title 102, and a color statement 103 referring to a color or set of colors. The title 102 indicates the stage of the menstrual cycle corresponding with the color of the color bar 101. According to one possible embodiment, the color bar 101 is divided into portions of different colors. According to one embodiment, the color bar 101 can be up to three of the following colors: pink 111, red 112, light blue 113, dark blue 114, stripes 115, gold 116, orange 117, brown 118, light purple 119, green 120, or dark purple 121 (See FIG. 2 where the colors of the color bars for different color definition entries are located on a date indicator, which will be further described.)

One embodiment of the color definition entry 100 further includes a duration indicator 104 indicating the length of time each stage persists. Another embodiment of the color definition entry 100 further includes textual information 105 regarding the stage of the menstrual cycle indicated by the color bar 101. The textual information 105 includes information about physical and emotional changes the average woman experiences during each stage of the menstrual cycle. The textual information 105 is arranged according to headings 106. Any desired number of headings 106 may be included in a color definition entry, depending on space and the amount of information one wishes to convey. Generally, between two and twenty headings 106 are included for each color definition entry 100. Typically, about twelve headings 106 are included for each color definition entry 100.

At a minimum, a color definition entry 100 defines a color as indicating a stage of a cycle, such as a menstrual cycle. Therefore, one embodiment of a color definition entry 100 only includes a title 102 and a color statement 103, or a title 102 and a color bar 101, without any of the other elements shown in FIG. 1. The term color definition entry refers to a set of information presented with a color, which may be limited to a name of a stage or may include some or all of the other types of information illustrated in FIG. 1.

In one embodiment that will be discussed in greater detail herein, each color definition entry 100 is printed on a card 1 or multiple cards 1 (see FIGS. 4-9). It is also possible for the color definition entry 100 to be presented on many different media types, such as a poster, a sheet of paper, or a computer screen. A poster or sheet of paper might show all of the color definition entries 100 on one piece of media. Alternatively, the different color definition entries 100 may each be present on separate pieces of media, as they are for the key card embodiment.

Another embodiment of the present disclosure includes a date indicator that enables a user to indicate and thereby record the stage of the menstrual cycle she is currently experiencing on a particular date for each date of a calendar year. According to one embodiment, the user indicates the current stage of her menstrual cycle by marking one of multiple choices, such as different colors. According to another embodiment, the user indicates the current stage of her menstrual cycle via writing text in a markable area. According to one embodiment, the date indicators include a list of calendar dates. According to yet another embodiment, each date indicator indicates a particular moon phase and includes dates occurring during that moon phase.

Figure 2:
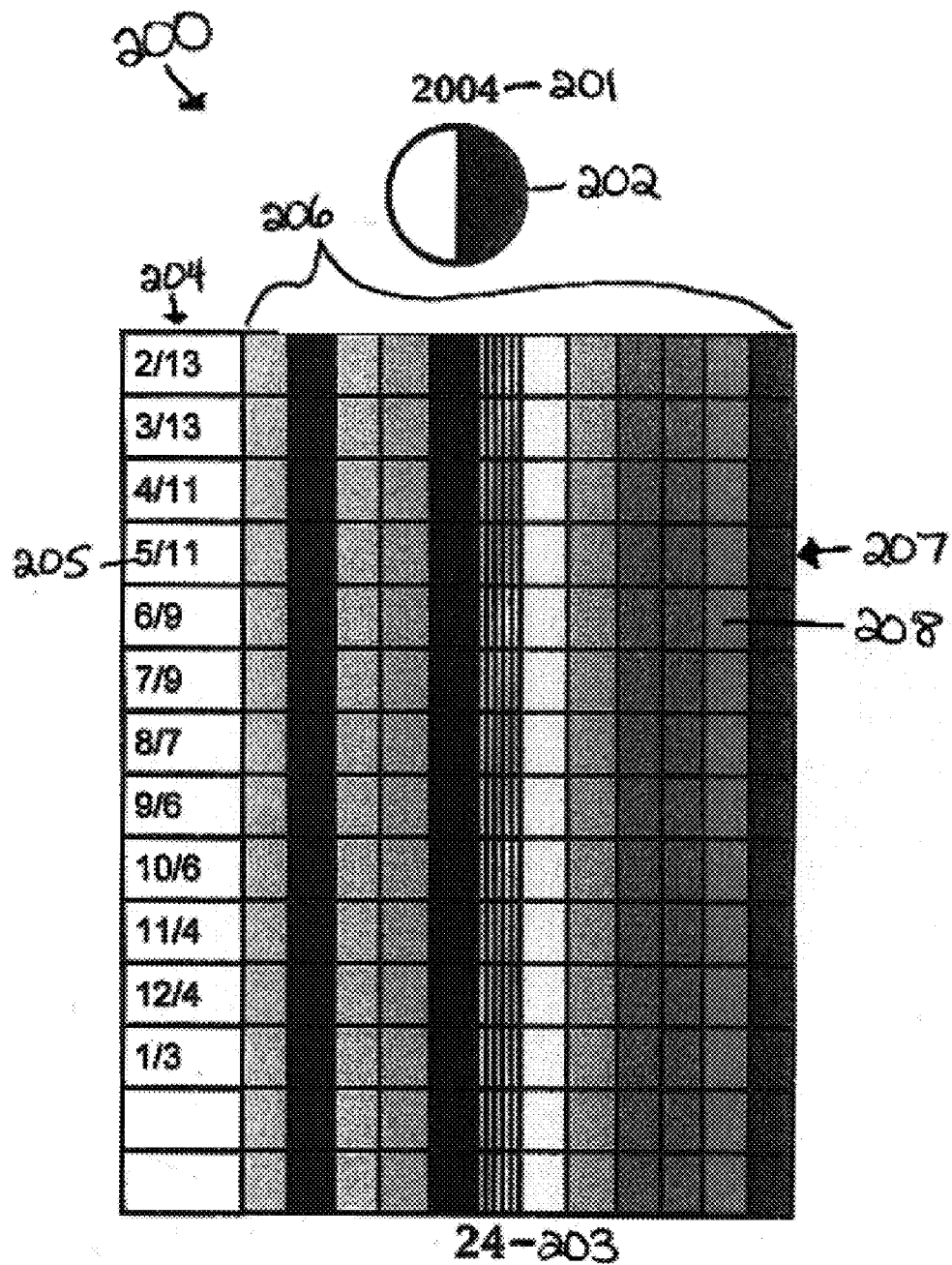
FIG. 2 illustrates a date indicator according to one possible embodiment of the present invention.

Referring to FIG. 2, a date indicator 200 according to one embodiment of the present disclosure is illustrated. Each date indicator 200 includes a calendar year 201 and visual indicia of a moon phase 202. Each date indicator 200 further includes a date section 204 listing a plurality of calendar dates 205 on which the indicated moon phase 202 will occur during the calendar year 201. A markable section 206 of the date indicator 200 includes a plurality of arrays 207 of colored boxes 208 arranged in sequence, each array 207 corresponding to a date 205 listed in the date section 204. Each colored box 208 is one of the eleven colors 111-121. Each array 207 on each date indicator 200 has the same sequence of colored boxes 208.

Each woman's menstrual cycle, while following the same basic format, differs in the duration of and the exact physical and emotional changes occurring during each stage. In order to enable a user to more accurately record her own reactions to each stage of her menstrual cycle, more than one color 111-121 can sometimes correspond to a stage. Each color 111-121 corresponds with different physical reactions that may occur during that stage. Each day, the woman chooses the color 111-121 representing the menstrual stage that best reflects the way her body is changing and marks that box 208 on the date indicator 200. In this way, the user is accorded flexibility and freedom in describing her specific physical and emotional changes to each stage. The user refers to the information provided in the color definition entries 100 to learn about each stage and select a color for each day.

It should be noted that, while color is used throughout this description, other types of indicia could also be correlated to the different stages of the menstrual cycle in place of color. For example, pictures, symbols, patterns, or text could also be matched to a menstrual stage using a definition entry similar to the color definition entry of FIG. 1. These indicia would then be used to identify the markable sections 206 of the date indicator 200 and to refer to the corresponding menstrual stage.

Figure 3:
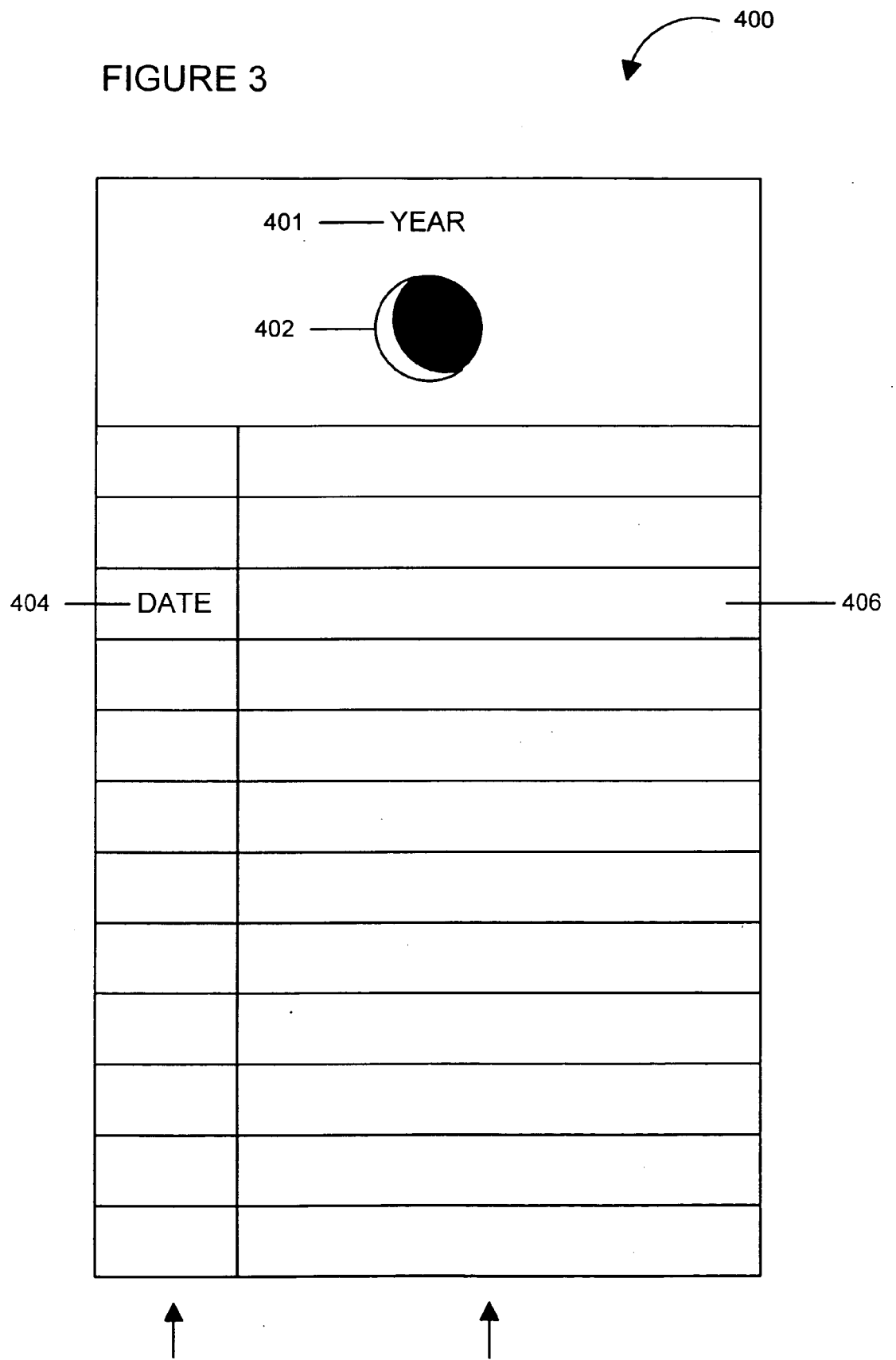
FIG. 3 illustrates a date indicator according to another possible embodiment of the present invention.

Referring to FIG. 3, a date indicator 400 according to another embodiment of the present disclosure is illustrated. Each date indicator 400 includes a calendar year 401 and visual indicia of a moon phase 402. Each date indicator 400 further includes a date section 403 and a markable section 405. According to one embodiment, the date section 403 includes a list of dates 404 that correspond to the moon phase 402. According to another embodiment, the date section 403 includes a plurality of spaces for writing in one or more calendar dates 404 corresponding with the moon phase 402. The markable section 405 includes a plurality of spaces 406 for indicating a stage of a menstrual cycle using text, symbols, patterns, pictures, colors, or other such indicia.

The term date indicator refers to the information that allows a user to make note of her current stage on a particular date. At a minimum, the date indicator 200, 400 includes a list of calendar dates 205, 404 and a markable area 206, 405. In one embodiment, the date indicator information is also arranged to help correlate Gregorian calendar dates 205, 404 with lunar cycles, such as by including a moon phase symbol 202, 402 and a list of dates 205, 404 corresponding to the moon phase symbol 202, 402 as discussed herein. One embodiment of a date indicator 200, 400 also includes a selection of markable areas 206, 405 to provide the user with a choice for recording her current stage. Another embodiment provides a space for recording the stage. The date indicator 200, 400 may be printed on a card 2 or on multiple cards 2 (see FIGS. 10-12), or may be portrayed on many other types of media, such as a poster, sheets of paper, or a computer screen.

One embodiment of the present disclosure divides the menstrual cycle into six stages. This embodiment includes a deck of cards. The deck of cards includes six (6) key cards, each displaying a color definition entry, one key card for each stage of the menstrual cycle. Each key card in the set includes visual indicia of a color or set of colors, wherein each color or set of colors corresponds with a stage of a woman's menstrual cycle. Each key card further includes information explaining physical and emotional changes to the female body generally occurring during the corresponding stage of the menstrual cycle. The deck of cards further includes a set of thirty-two (32) moon cards. Each moon card includes visual indicia of a moon phase and the Gregorian calendar dates that correspond to that moon phase.

Referring now to FIGS. 4-9, example color definition entries 10, 20, 30, 40, 50, 60 according to one possible embodiment of the present disclosure are illustrated. Each color definition entry 10, 20, 30, 40, 50, 60 is present on a key card 1 and corresponds to one of the stages of the menstrual cycle. Key cards 1 represent one way in which color definition entries 100 can be arranged and configured. The intent of this disclosure is not to limit color definition entries 100 to these particular embodiments 10, 20, 30, 40, 50, but merely to illustrate one way in which a color definition entries 100 could be embodied.

In this embodiment, each color definition entry 10, 20, 30, 40, 50, 60 includes information 105 regarding twelve areas in which a woman generally experiences changes during her menstrual cycle, each area denoted by a heading 106. The headings 106 include Vulva 151, Uterus 152, Cervix 153, Flow 154, Body 155, Breast 156, Core Temp 157, Ovary 158, Hormones 159, Cycle Time 160, Number of Day 161, and Status 162. The intention is not to limit the invention to these particular headings 106. Any number of areas regarding physical and emotional changes occurring during each stage may be covered within this textual section 105.

Still referring to FIGS. 4-9, the headings Vulva, Uterus, Cervix, Breast, and Ovary 151-153, 155, and 158 respectively, correspond with textual descriptions 105 regarding the physical changes in these areas of the body. The heading Flow 154 corresponds with a textual description 105 of the changes in texture and amount of the fluid-like mucus in/on the cervix, vagina, and vulva. The heading Body 155 corresponds with a description of the overall physical and emotional reactions that the average woman experiences during each stage. The heading Core Temp 157 corresponds with a description of the changes in the core temperature of the woman's body. A woman obtains a core temperature reading by taking her temperature at the same time each day. The heading Hormones 159 corresponds with a description of the female hormones active during the current stage. The heading Cycle Time 160 corresponds with a brief description of when this stage occurs in relation to ovulation and menstruation. The heading Number of Days 161 corresponds with a description of the duration of the stage. The heading Status 162 corresponds with a key word or phrase summing up the main idea or concept behind this division or stage in the cycle.

Referring now to FIG. 4, an example of a color definition entry 10 according to one embodiment of the present disclosure is illustrated. This color definition entry 10 corresponds to the first stage of a woman's menstrual cycle. While it is possible for a woman to begin using the key cards 1 during any stage of her menstrual cycle, it is generally easiest to begin on the first day of the menstruation stage. Therefore, for the purpose of this description, the menstruation stage is considered the first stage in the cycle.

The colors pink 111 and red 112 indicate the menstruation stage of the menstrual cycle. A color bar 11 of the color definition entry 10 is divided into three sections 11*a*, 11*b*, and 11*c*. Sections 11*a* and 11*c* are colored pink 111 and section 11*b* is colored red 112. The color red 112 indicates regular flow days and the color pink 111 indicates either light flow days or days on which the woman is spotting. The key card title 12 is MENSTRUATING. The textual representation of the color 13 is PINK/RED/PINK. The color definition entry 10 further includes textual information 15 regarding the average woman's physical and emotional reactions to this menstrual stage. The textual information 15 is arranged according to headings 16.

Referring now to FIG. 5, an example of a color definition entry 20 corresponding to the second stage of a woman's menstrual cycle according to one embodiment of the present disclosure is illustrated. According to one embodiment, the second stage refers to the time immediately following the menses. The color bar 21 is light blue 113 and the key card title 22 is NOT WET YET. The textual representation of the color 23 is LIGHT BLUE. The color definition entry 20 further includes textual information 25 regarding the average woman's physical and emotional reactions to this menstrual stage. The textual information 25 is arranged according to headings 26.

Referring to FIG. 6, an example of a color definition entry 30 corresponding to the third stage of a woman's menstrual cycle according to one embodiment of the present disclosure is illustrated. The third stage refers to the time preceding ovulation. The color bar 31 is divided into two sections 31*a*, 31*b*. Section 31*a* is dark blue 114 and section 31*b* is striped 115 blue and white. The dark blue 114 color indicates watery mucus secretions and the stripes 115 indicate slippery, elastic or thread-like mucus secretions. The key card title 32 is WET. The textual representation of the color 33 is DEEP BLUE/STRIPES. The color definition entry 30 further includes textual information 35 regarding the average woman's physical and emotional reactions to this menstrual stage. The textual information 35 is arranged according to headings 36.

Referring to FIG. 7, an example of a color definition entry 40 corresponding to the fourth stage of a woman's menstrual cycle according to one embodiment of the present disclosure is illustrated. The fourth stage refers to the time when the woman is ovulating. The color bar 41 is gold 116 and the key card title 42 is OVULATING. The textual representation of the color 43 is GOLD. The color definition entry 40 further includes textual information 45 regarding the average woman's physical and emotional reactions to this menstrual stage. The textual information 45 is arranged according to headings 46.

Referring to FIG. 8, an example of a color definition entry 50 corresponding to the fifth stage of a woman's menstrual cycle according to one embodiment of the present invention is illustrated. The fifth stage refers to the time after ovulation. The color bar 51 is divided into two sections 51*a*, 51*b*. Section 51*a* is orange 117 and section 51*b* is brown 118. The color orange 117 indicates pasty mucus secretions and the color brown 118 indicates no mucus secretions. The key card title 52 is AFTER OVULATION. The textual representation of the color 53 is ORANGE/BROWN. The color definition entry 50 further includes textual information 55 regarding the average woman's physical and emotional reactions to this menstrual stage. The textual information 55 is arranged according to headings 56.

Referring to FIG. 9, an example of a color definition entry 60 corresponding to the sixth stage of a woman's menstrual cycle according to one embodiment of the present disclosure is illustrated. The sixth stage refers to the time immediately preceding menstruation. The color bar 61 is divided into three sections 61*a*, 61*b*, and 61*c*. Section 61*a* is light purple 119, section 61*b* is green 120, and section 61*c* is dark purple 121. The key card title 62 is TRANSITION. The textual representation of the color 63 is PURPLE/GREEN. The color definition entry 60 further includes textual information 65 regarding the average woman's physical and emotional reactions to this menstrual stage. The textual information 65 is arranged according to headings 66.

Figure 10:
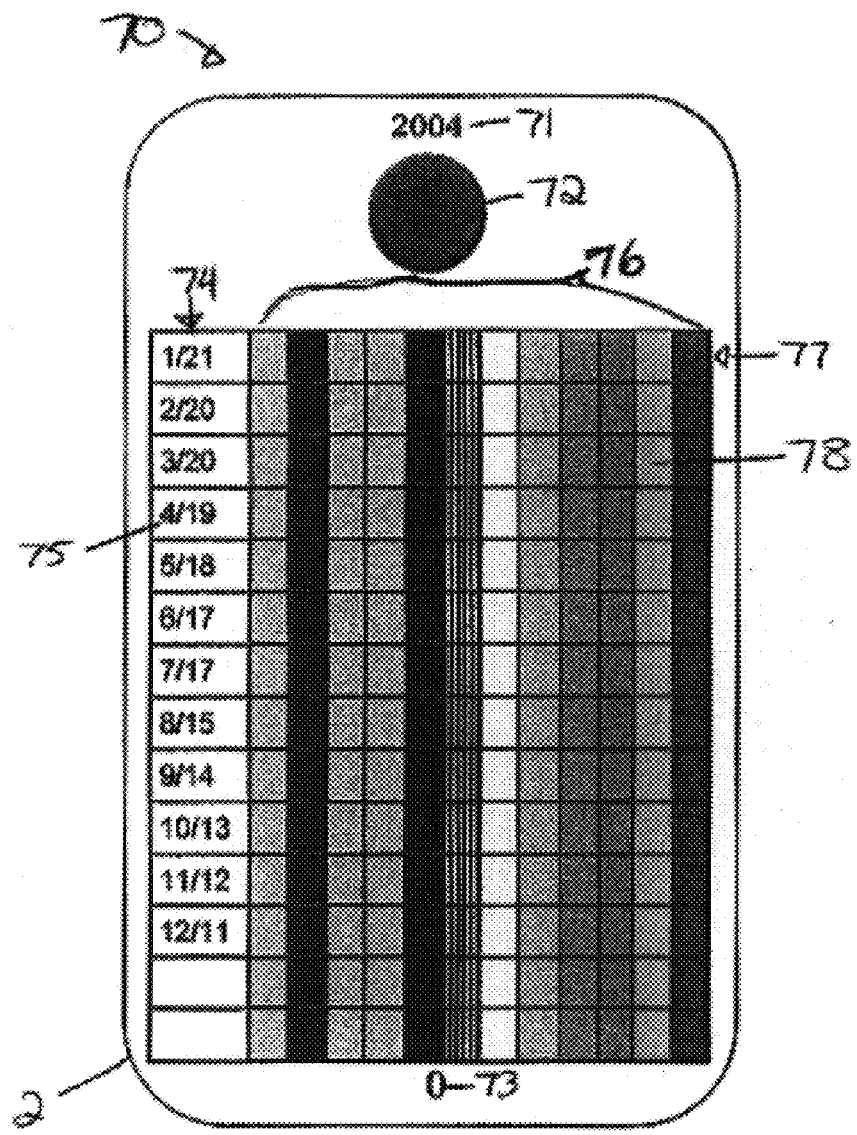
FIG. 10 illustrates an example of a date indicator present on a moon card according to one embodiment of the present invention.
Figure 11:
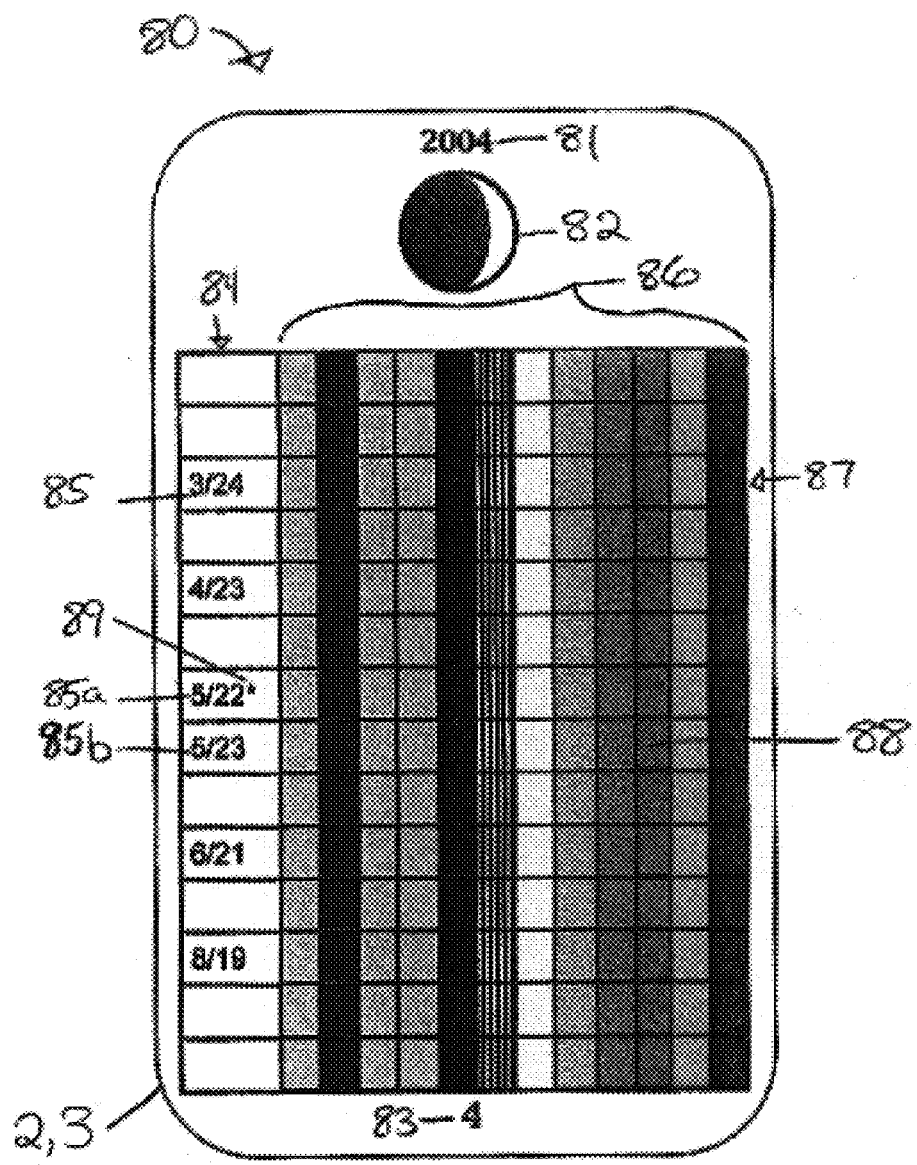
FIG. 11 illustrates an example of a wobble date indicator present on a moon card according to one embodiment of the present invention.
Figure 12:
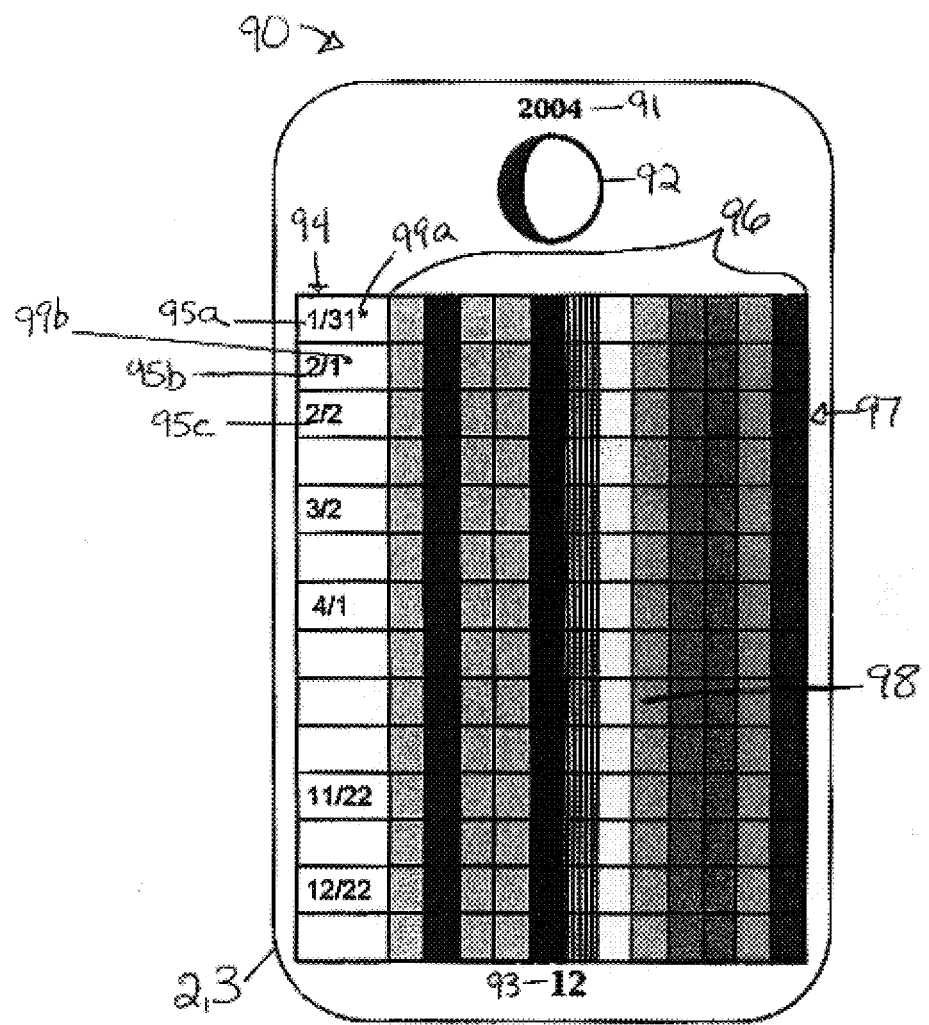
FIG. 12 illustrates another example of a wobble date indicator present on a moon card according to another embodiment of the present invention.

Referring now to FIGS. 10-12, example date indicators 70, 80, 90 according to one possible embodiment of the present disclosure are illustrated. Each date indicator 70, 80, 90 is present on a moon card 2. One feature of the present invention is that it correlates the menstrual cycle to the lunar cycle rather than a Gregorian calendar. The average woman's cycle lasts between twenty-five and twenty-eight days. A synodic month, which is the duration of time between two new moons, takes twenty-nine and one half days to complete instead of the thirty to thirty-one days of each Gregorian month. Therefore, the moon cards 2 are arranged according to the phases of the moon instead of the months of the year.

However, since creating twenty-nine and one half moon cards 2 would be impractical, one embodiment of the present disclosure includes thirty-two moon cards 2. These moon cards 2 include visual indicia of a moon phase 202. Generally, the quarter phases of the moon (i.e. new moon, first quarter, full moon, and third quarter) occur on the first, ninth, seventeenth, and twenty-fifth moon cards 2. This allows for a nine-day transition period between one quarter phase and the next. However, the elliptical orbit of the moon causes the number of days between moon quarters to vary, meaning that between six and nine days will pass between one moon quarter and the next. To accommodate this variability, four of the moon cards 2 are wobble cards 3.

Wobble cards 3 generally include a date 205 for only some of the months of the calendar year 201. One embodiment of a wobble card 3 includes two consecutive dates 205. Another embodiment of a wobble card 3 includes three consecutive dates 205. The number of consecutive dates 205 included on a wobble card 3 will depend on how many days it takes to get from one moon quarter to the next. In particular, if only six days will pass from one quarter to the next, then the wobble card 3 will not contain a date 205 occurring during that quarter. If seven days will pass, then the wobble card 3 will include one date 205 occurring during that quarter. If eight days will pass, then the wobble card 3 will contain two consecutive dates 205 for that quarter. Finally, if nine days will pass between one quarter phase and the next quarter phase, then the wobble card 3 will include three consecutive dates 205 for that quarter. Some moon cards 2, which are not wobble cards 3, will also include dates 205 for only some months of the calendar year 201. Some other moon cards 2, which are not wobble cards 3, include two dates 205 within one Gregorian month, but not consecutive dates 205.

Generally, because the moon cards 2 are configured for a specific calendar year 201, 401, a new set of moon cards 2 is created and sold to a user each calendar year 201, 401. It is within the scope of the invention, however, that a date indicator 200, 400 or set of date indicators 200, 400 may be configured so not to correlate with a particular calendar year 201, 401. For example, one embodiment of a date indicator 200, 400 allows the user to write in the corresponding Gregorian calendar dates 205, 405 for each moon phase 202, 402.

Another embodiment of the date indicators 200, 400 follows a school year or a year beginning with the summer solstice instead of a calendar year 201, 401.

Referring now to FIG. 10, an example of a date indicator 70 according to one embodiment of the present disclosure is illustrated. The example date indicator 70 includes a date year 71 and a moon phase indicia 72. The moon phase indicia 72 illustrates a black circle indicating a new moon. The moon card number 73 depicts the number zero. According to one embodiment of the present invention, moon cards 2 are numbered zero through thirty-one starting on the moon card 2 corresponding with the new moon. Each date of the year is present on one of the thirty-two moon cards 2. Each moon phase is depicted on one of the thirty-two moon cards 2.

The date indicator 70 further includes a date section 74 and a tracking section 76. The date section 74 includes a plurality of dates 75 on which a new moon will occur. On this particular date indicator 70, only one date 75 for each month is present and none of the dates 75 are consecutive. The tracking section 76 includes a plurality of arrays 77 of colored boxes 78. Each array 77 of colored boxes 78 corresponds with a date 75 listed in the date section 74. The boxes 78 are each one of the eleven possible colors 111-121 and are arranged so that boxes 78 of the same color 111-121 occupy the same location on each of the arrays 77.

Referring now to FIGS. 11 and 12, examples of additional date indicators 80, 90 are illustrated. Date indicators 80, 90 are present on wobble cards 3. A wobble card 3 is a special type of moon card 2. Referring to FIG. 11, date indicator 80 includes a calendar year 81, moon phase indicia 82, and moon card number 83. The moon phase indicia 82 illustrates a mostly black circle, a crescent shaped portion of which is colored white on the right hand side, indicating a waxing crescent. Date indicator 80 further includes a date section 84 and markable section 86. Date indicator 80 differs from date indicator 70 in that the date section 84 of date indicator 80 generally includes fewer dates 85. Furthermore, the date section 84 of date indicator 80 includes two consecutive dates 85a, 85b, respectively. In other words, date 85b immediately follows date 85a on the Gregorian calendar. According to one embodiment, a wobble marker 89 is displayed adjacent to the first date 85a of the two consecutive dates 85a, 85b to indicate to the user that she should use the wobble card 3 displaying date indicator 80 two days in a row.

Referring to FIG. 12, date indicator 90 includes a calendar year 91, moon phase indicia 92, and moon card number 93. The moon phase indicia 92 illustrates a mostly white circle, a crescent shaped portion of which is colored black on the left hand side, indicating a waxing gibbous. Date indicator 90 further includes a date section 94 and markable section 96. Date indicator 90 differs from date indicator 80 in that the date section 94 of date indicator 90 includes three consecutive dates 95a, 95b, and 95c respectively. In other words, 95b immediately follows date 95a and immediately precedes date 95c on the Gregorian calendar. According to one embodiment, the first date 95a and the second date 95b include wobble markers 99a, 99b, respectively to indicate to the user that the wobble card 3 displaying date indicator 90 should be used three days in a row. According to one embodiment, wobble marker 99b is the same as wobble marker 99a. According to another embodiment, wobble marker 99b is depicted differently from wobble marker 99a.

Referring back to FIGS. 4-12, generally, the key cards 1 and moon cards 2 are the same size and shape. According to one embodiment, the key cards 1 and moon cards 2 are rectangular. It is also possible for the key cards 1 and the moon cards 2 to have any desired shape or to each have a different shape. Generally, the key cards 1 and moon cards 2 range in size from one and one half (1.5) inches by two and one half (2.5) inches (to fit inside a purse or wallet) to six (6) inches by ten (10) inches (to allow for larger print). Typically, the key cards 1 and moon cards 2 are three inches by five inches.

According to one embodiment, each of the key cards 1 and each of the moon cards 2 are separated from each other. Another embodiment of the key cards 1 includes one or more color definition entries 100 per key card 1. Another embodiment of the moon cards 2 includes one or more date indicators 200, 400 per moon card 2. According to one embodiment, the key cards 1 and moon cards 2 are printed on stiff paper and are stackable. According to another embodiment, the key cards 1 and moon cards 2 are printed on transparencies, printer paper, or other such media. According to yet another embodiment, the key cards 1 and moon cards 2 are displayed on a computer screen.

Figure 13:
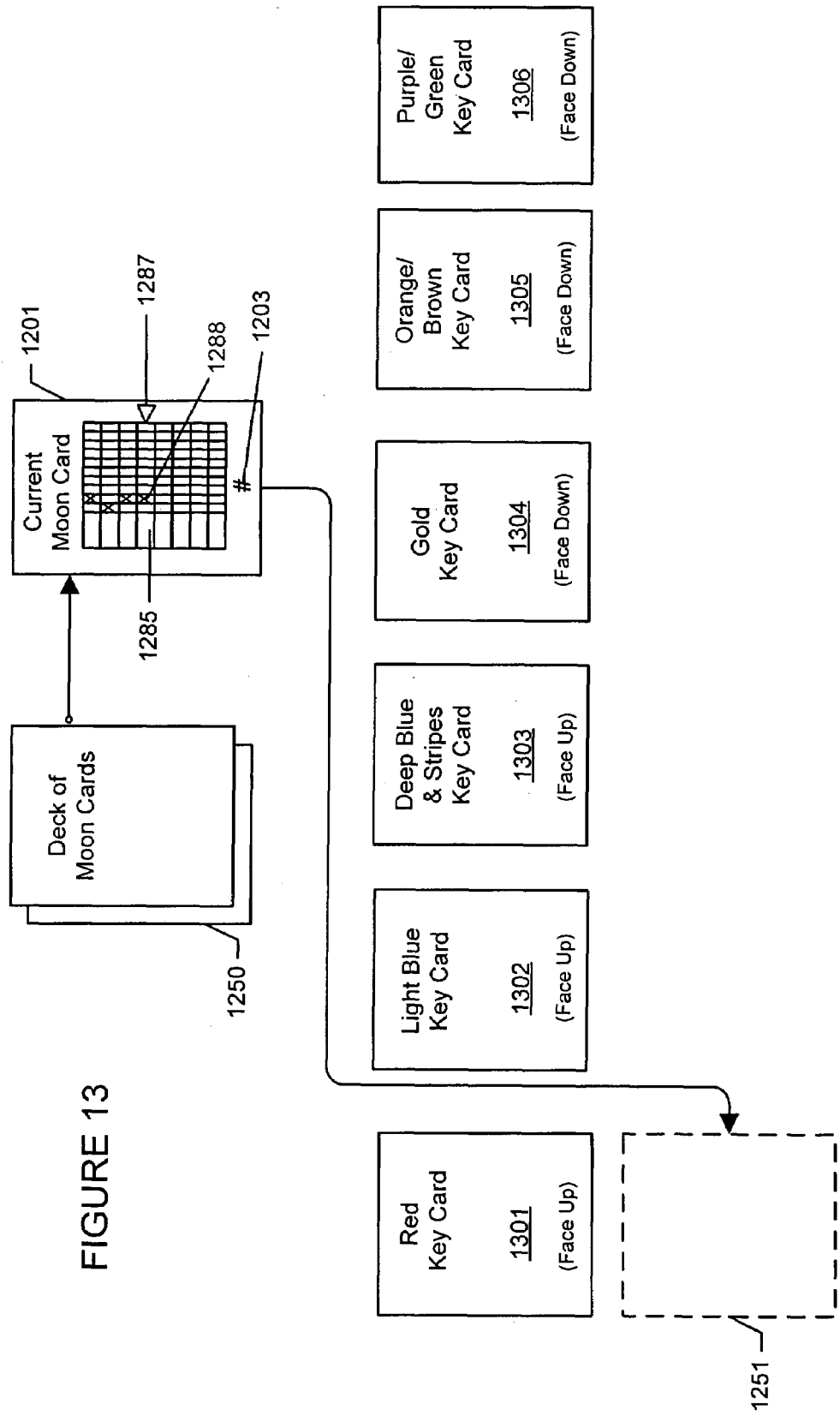
FIG. 13 illustrates an example layout of moon cards and key cards, as it would look during use in one embodiment if the user were beginning the first stage (or menstruation stage) of her menstrual cycle.
Figure 14:
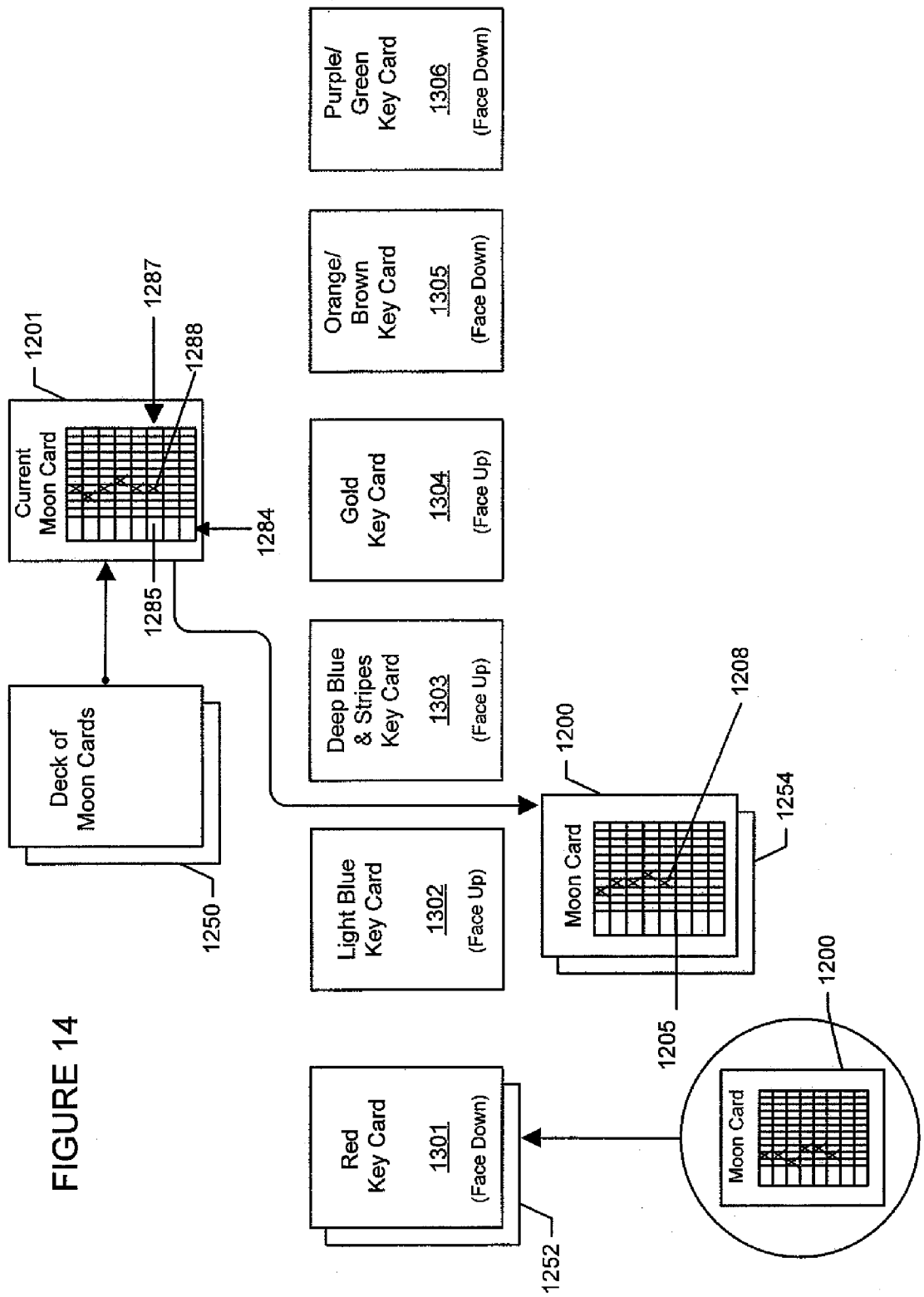
FIG. 14 illustrates an example layout of moon cards and key cards, as it would look if the user were in the second stage (or Not Wet Yet stage) of her menstrual cycle.
Figure 15:
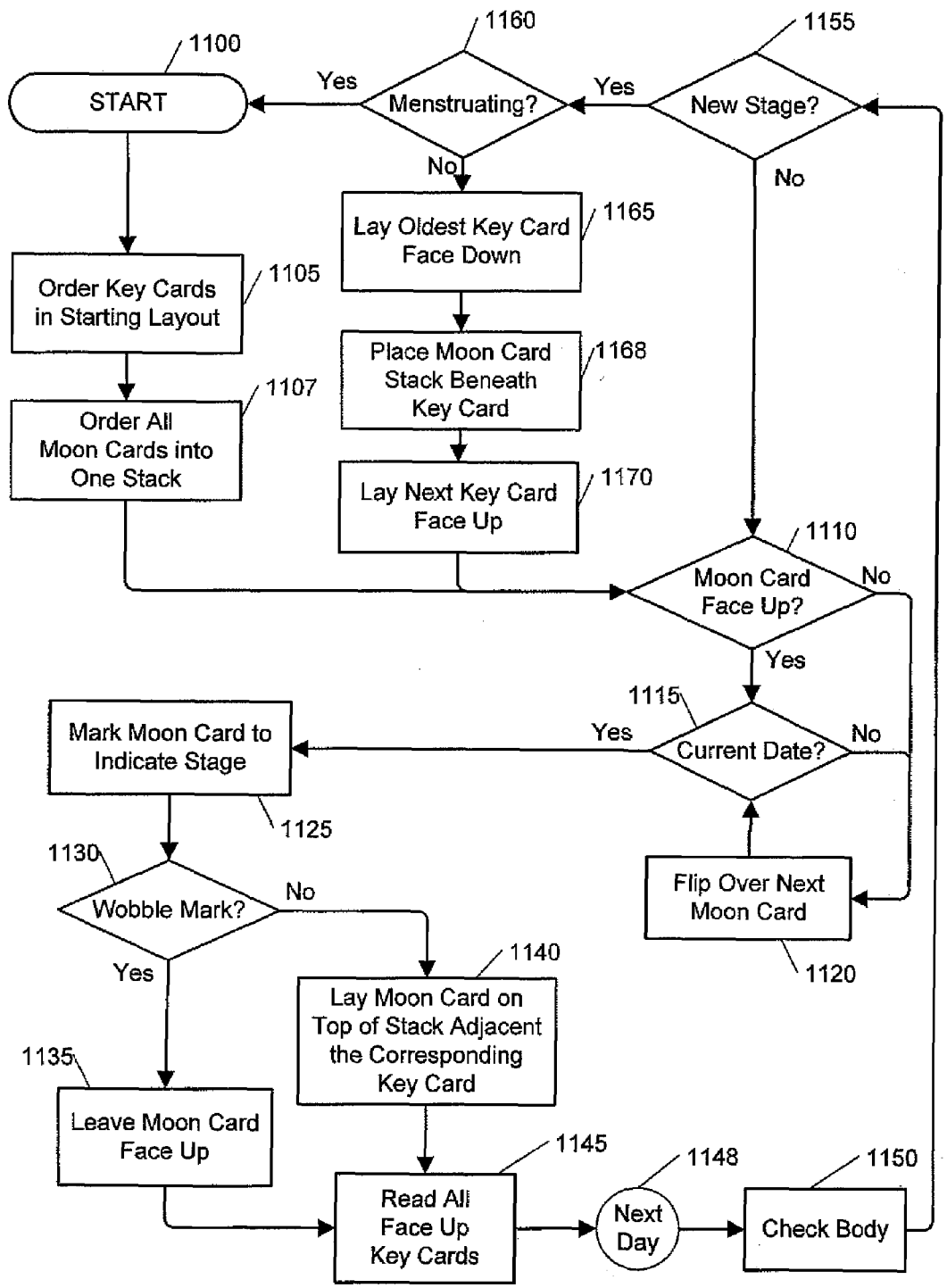
FIG. 15 illustrates a flow chart depicting a method for using the index entries and date indicators of the present invention.

Referring now to FIGS. 13-15, a method for tracking and learning about a woman's menstrual cycle utilizing moon cards 1200 and key cards 1300 is illustrated. The moon cards 1200 and six key cards 1301-1306 are used in playing a calendar card game. Each moon card 1200 generally resembles one of the date indicators 70, 80, 90 shown in FIGS. 10-12. Each key card 1301-1306 generally resembles one of the color definition entries 10, 20, 30, 40, 50, 60 depicted in FIGS. 4-9.

Referring to FIG. 13, an example layout for moon cards 1200 and key cards 1300, as it would look if the user were beginning the first stage of her menstrual cycle, is shown. The six key cards 1301-1306 are arranged in sequential order with the fourth 1304, fifth 1305, and sixth 1306 key cards laying face down. The first 1301, second 1302, and third 1303 key cards are laying face up. The moon cards 1200 are arranged in a stack 1250 and a current moon card 1201 has been flipped over to lay face up next to the stack 1250. The stack 1250 is arranged so that the moon cards 2 can be flipped over in numeral order. The date section 1284 of the current moon card 1201 includes a date 1285 corresponding with the current date. Once marked, the current moon card 1201 is placed adjacent to the first key card 1301. This is shown by the broken-line outline 1251 of a moon card 1200 below the first key card 1301.

Referring to FIG. 14, an example layout for moon cards 1200 and key cards 1301-1306, as it would look if the user were currently part of the way through the second stage of her menstrual cycle, is shown. The six key cards 1301-1306 are arranged in sequential order with the first 1301, fifth 1305, and sixth 1306 key cards laying face down. The second 1302, third 1303, and fourth 1304 key cards are laying face up. The moon cards 1200 are arranged in a stack 1250 and a current moon card 1201 has been flipped over to lay face up next to the deck 1250. The date section 1284 of the current moon card 1201 includes a date 1285 corresponding with the current date.

According to one embodiment, the first key card 1301 has a separate stack 1252 of moon cards 1200 beneath it. The most recent date 1285 of each moon card 1200 in the stack 1252 is marked to indicate the first stage of the menstrual cycle. In other words, the bottom-most marked box 1288 on each moon card 1200 in the stack 1252 is either pink 111 or red 112. According to one embodiment, the second key card 1302 has a stack 1254 of moon cards 1200 adjacent to it. The bottom-most marked box 1288 on each moon card 1200 in the stack 1254 is light blue 113.

Generally, for each stage of the menstrual cycle, a user stacks up the moon cards 1200 indicating the user's current stage adjacent to the key card 1300 corresponding to the stage. This way, the moon cards 1200 corresponding to the current stage are visible throughout the duration of the stage. When the user proceeds to the next key card 1303 in the example depicted in FIG. 14, the moon cards 1200 in stack 1254 will be placed beneath key card 1302 so that they are no longer visible. The user will then begin placing the moon card 1200 marked each day of the third stage into a stack adjacent key card 1303. According to another embodiment, the stack 1254 of moon cards 1200 is located beneath key card 1302, similar to stack 1252 and key card 1301.

Referring now to FIG. 15, an operational flow chart depicting a method for tracking and informing about a woman's menstrual cycle utilizing the moon cards 1200 and key cards 1301-1306 is shown. Throughout the description of this figure, the "face" of a key card refers to the side of the key card on which the color bar and textual information is displayed. The "face" of a moon card refers to the side of the moon card on which the arrays of colored boxes are displayed. Generally, the flow chart will be described with reference to the layouts shown in FIGS. 13 and 14.

The process starts at module 1100 and proceeds to operations 1105 in which the user orders the key cards 1301-1306 according to color and lays them face down in sequence. The user then flips over the first, second, and third key cards 1301, 1302, 1303, respectively so that they lay face up. In operation 1107, all of the moon cards 1200 are sorted into one ordered stack 1250, separate from the key cards 1301-1306. The moon cards 1200 in stack 1250 have been ordered face down by moon card number 1203 with the moon card 1201 corresponding with the current date 1285 on top of the stack 1250. At this point, the layout of the moon cards 1200 and key cards 1301-1306 resembles the layout depicted in FIG. 13.

The process then proceeds to operation 1110. Operation 1110 requires the user to make a determination as to whether a moon card 1200 is already laying face up. If a moon card 1200 is already laying face up, then at operation 1115, the user must make another determination. The user must determine whether the moon card 1200 includes the current date 1285 and is therefore the current moon card 1201. If the moon card 1200 is not the current moon card 1201, meaning that it does not include the current date 1285, or if a moon card 1200 was not laying face up in operation 1110, then the process proceeds to operation 1120.

Operation 1120 requires the user to flip over the next moon card 1200 in the deck 1250. This operation then leads back to operation 1115 in which the user checks the moon card 1200 to see if it has the current date 1285. The user continues looping between operations 1115 and 1120 until she finds the moon card 1201 including the current date 1285. Because the moon cards 1200 are ordered according to moon card number 1203 in operation 1107, the user will only need to loop a few times, if any. The moon cards 1200 not having the current date 1285 are stacked adjacent to the key card 1300 corresponding to the most recently used moon card 1200. For example, in FIG. 14, if the current moon card 1201 did not have the current date 1285, then it would have been placed on top of stack 1254.

When the moon card 1201 includes the current date 1285, then the process proceeds to operation 1125. In operation 1125, the user marks the current moon card 1201 to indicate her current menstrual stage. For example, if the user were in her first menstrual stage, as in FIG. 13, then she would mark either the pink 111 or red 112 box 1288 in the array 1287 that corresponds with the current date 1285. If the user were in her second menstrual stage, as in FIG. 14, then she would mark the light blue 113 box 1288 in the array 1287.

Next, operation 1130 requires the user to make yet another determination. The user must determine whether a wobble marker 89, 99 (FIGS. 11 and 12) is adjacent to the current date 1285 on her current moon card 1201. In other words, the user must determine whether the date of the following day corresponds with the next date 1285 listed on the moon card 1201. If the user determines that such a marker 89, 99 is adjacent to the current date 1285, then, in operation 1135, the user leaves the moon card 1201 laying face up.

If the user determines that the current date 1285 is not marked in this way, then the process proceeds to operation 1140 in which the moon card 1201 is laid beneath the key card 1300 corresponding to the stage marked on the moon card 1201. For example, if the user marked the light blue 113 box 1288, then she would place the moon card 1201 in the stack 1254 adjacent to the second key card 1302, which corresponds with the color light blue 113. In this way, during each stage, the user builds stacks of moon cards 1200 adjacent the key card 1300 representing her current stage. Both operations 1135 and 1140 lead to operation 1145 in which the user studies all of the key cards 1300 that are laying face up.

This operation leads to module 1148, which indicates that the user performs the operations following the module on the following day. In particular, operation 1150 includes the user checking her body for the physical and emotional changes listed on the three key cards 1300 laying face up. Operation 1155 requires the user to make a determination. The user must decide whether her physical and emotional reactions have changed from the previous day, indicating that she has moved into a new stage of her menstrual cycle. If the user determines that she has not entered a new stage of her menstrual cycle, then she proceeds back to operations 1110. If the user determines that she has entered a new stage, then she proceeds to operation 1160. Operation 1160 requires the user to make a determination. The user must decide whether or not the new stage she has just begun is the menstruation stage.

If the user determines that she has begun a new stage, but that the new stage is not her menstrual cycle, then she proceeds to operation 1165. In operation 1165, the user flips over the oldest key card 1300, meaning the key card corresponding to the stage that just ended, so that it lays face down. Next, in operation 1168, the user places the stack of moon cards 1300, which she built adjacent to the oldest key card 1300, beneath the oldest key card 1300. In operation 1170, the user flips over the next key card 1300 in the sequence and lays it down face up. For example, in the layout shown in FIG. 14, the fifth key card 1305 would be the next key card 1300 to be flipped over. The second key card 1302 would be flipped to lay face down. This way, at any given time, the user will only have a limited number of key cards 1300 with which she will need to be familiar. Operation 1170 leads back to operation 1110 discussed above.

Referring back to operation 1160, if the user determines that the new stage is her menstruation stage, then the process proceeds back to the start module 1100 and the user begins the cycle again. Because this flow chart depicts a cycle, the process does not terminate at any specific point, but always returns to operation 1100. The user will continue the process each day until she chooses to discontinue. Because the duration of each stage differs from woman to woman, it is possible that a woman may run out of moon cards 1200 before her menstruation cycle begins again. In this case, she should combine all of her moon cards 1200 back into one stack 1250 when necessary.

This method depicts one way in which the color definition entries 100 and date indicators 200 could be used. This disclosure is not meant to limit the invention to this particular use. Rather, the description was meant to be merely illustrative. According to one embodiment of this disclosure, the color definition entries 100 are displayed on a poster or desk chart instead of on separate key cards 1. According to another embodiment, the markable sections 206 of the date indicators 200 are combined together on one poster or chart. According to yet another embodiment, both the color definition entries 100 and the date indicators 200 are included on one poster or chart. According to still yet another embodiment, the date indicators 200 are each on separate pages on a tear off calendar or wall hanging.

According to another embodiment, the user could also use the color definition entries 100 separately from the date indicators 200. For example, merely reading through the information on the color definition entries 100 is useful to a user. According to yet another embodiment, the user completes only operations 1145-1170 each cycle instead of the entire process. According to yet another embodiment, the user uses the date indicators 200 to complete only operations 1110-1140 without consulting the color definition entries 100. According to still yet another embodiment, the user cycles through the process using the date indicators 400 as shown in FIG. 3.

While the primary topic of this disclosure, the menstrual cycle is not the only timeframe over which a woman experiences bodily changes that can be broken down into stages. Pregnancy is another example of a time when a woman undergoes great physical changes. The gestation period can also be broken down into stages or phases. Color definition entries 100 and date indicators 200, 400 can be used to convey large amounts of information about each of these stages in an easy to understand and easy to reference format.

The systems and methods described in this disclosure could also be used for educating about and tracking other health and body phases and characteristics, especially those of a cyclical nature. In particular, date indicators 200, 400 would be useful for tracking cyclical changes in a person's physical, emotional, and physiological states, especially if these changes are affected by the lunar cycle. For example, the date indicator 400 of FIG. 3 could be used to track the moon's effect on mood swings by textually recording the moods of the user on the markable section 405 each day 404. The date indicator 200 of FIG. 2 could also be used for this purpose with some minor modifications within the spirit and scope of the invention (e.g. associate a particular mood with a particular color).

The various embodiments described above are provided by way of illustration only and should not be construed to limit the invention. Those skilled in the art will readily recognize various modifications and changes which may be made to the present invention without strictly following the exemplary embodiments and applications illustrated and described herein and without departing from the true spirit and scope of the present invention which is set forth in the following claims.

The claimed invention is:

1. A method for tracking and informing about a menstrual cycle of a woman comprising the steps of:
    (a) providing a plurality of color definition entry cards, each color definition entry card defining a color as representing a stage of the menstrual cycle;
    (b) providing a plurality of tracking cards having date indicators, each date indicator including a date section and a tracking section corresponding to each date section, wherein the date section indicates at least one date, wherein the tracking section is capable of being marked so as to indicate one of the colors for which there is a color definition entry card to signify the stage of the menstrual cycle for each date;
    (c) positioning one of the plurality of tracking cards face up to be a current date indicator card;
    (d) positioning one of the plurality of color definition entry cards face up to be a current color definition entry card;
    (e) marking the tracking section of the current date indicator card, to indicate one of the colors for which there is a color definition entry card positioned face up, to signify the woman's stage of the menstrual cycle for a current date.

2. The tracking method of claim 1 further comprising the step of positioning the plurality of color definition entries in sequential order by the stage of the menstrual cycle that is represented by each color.

3. The tracking method of claim 1 further comprising the steps of positioning two additional color definition entry cards face up, where the two additional color definition entry cards signify stages of the menstrual cycle that occur after the stage of the menstrual cycle represented by the current color definition entry card.

4. The tracking method of claim 1, wherein the date indicators are grouped into a plurality of date groupings according to a phase of the moon that will be occurring on the dates in the grouping.

5. The tracking method of claim 4, wherein each date grouping of date indicators are printed on a separate tracking card, wherein each tracking card includes visual indicia representing the moon phase that will be occurring on the dates indicated on the date indicator card.

6. The tracking method of claim 1, wherein the tracking section of each date indicator includes an array of boxes.

7. The tracking method of claim 1, wherein each box in the array is a colored box where the color of the box corresponds with the color of a color definition entry.

8. A method for tracking and informing about a reproductive system, the method comprising:
    (a) providing a plurality of color definition entry cards, each color definition entry card defining a color as representing a stage of a reproductive process
    (b) providing a plurality of tracking cards comprising date indicators, each date indicator including a date section and a tracking section corresponding to each date section, wherein the date section indicates one date, wherein the tracking section is capable of being marked so as to indicate one of the colors for which there is a color definition entry to signify the stage of the reproductive process for each date, wherein each markable area includes an array of colored sections, wherein each color of each section corresponds to one of the stages of the reproductive process;
    (c) positioning one of the plurality of tracking cards face up to be a current date indicator card;
    (d) positioning one or more of the plurality of color definition entries face up; and
    (e) marking the tracking section of the current date indicator card, to indicate one of the colors for which there is a color definition entry card positioned face up, to signify a stage of the reproductive process.

9. The method of claim 6 wherein:
    each color definition entry defines the color as representing a stage of pregnancy.

10. A method for tracking and informing about a menstrual cycle of a woman, the system comprising:

(a) providing a plurality of color definition entries, each color definition entry defining a color as representing a stage of the menstrual cycle, wherein the color definition entries define:
   a first color for ovulation,
   a second color for menstruation,
   a third color for a first stage that occurs in time after menstruation and before ovulation, and
   a fourth color for a second stage that occurs in time after menstruation and before ovulation,
   wherein the first color is not used to indicate the first or second stage;
   wherein the third color is not used to indicate ovulation or the second stage;
   wherein the fourth color is not used to indicate ovulation or the first stage;
(b) providing a plurality of date indicators, each date indicator including a date section and a markable area corresponding to each date section, wherein the date section indicates at least one date, wherein each markable area is capable of being marked so as to indicate one of the colors for which there is a color definition entry to signify the stage of the menstrual cycle for each date;
(c) positioning one of the plurality of date indicators to be a current date indicator;
(d) positioning one of the plurality of color definition entries to be a current color definition entry; and
(e) marking the tracking section of the current date indicator, to indicate the color of the current color definition entry, to signify the woman's stage of the menstrual cycle for a current date.

11. The tracking method of claim 10, wherein the date indicators are grouped into a plurality of date groupings according to a phase of the moon that will be occurring on the dates in the grouping.

12. The tracking method of claim 11, wherein each date grouping of date indicators are printed on a separate tracking card, wherein each tracking card includes visual indicia representing the moon phase that will be occurring on the dates indicated on the tracking card.

13. The tracking method of claim 10, wherein the tracking section of each date indicator includes an array of boxes.

14. The tracking method of claim 13, wherein each box in the array is a colored box where the color of the box corresponds with the color of a color definition entry.

* * * * *